(12) United States Patent
Munro et al.

(10) Patent No.: US 6,792,301 B2
(45) Date of Patent: Sep. 14, 2004

(54) BIOADHESIVE COMPOSITIONS AND BIOMEDICAL ELECTRODES CONTAINING THEM

(75) Inventors: Hugh Semple Munro, Chipping Camden (GB); Mohammed Yasin, Saltley (GB)

(73) Assignee: First Water Limited, Marlborough (GB)

( * ) Notice: Subject to any disclaimer, the term of this patent is extended or adjusted under 35 U.S.C. 154(b) by 0 days.

(21) Appl. No.: 10/301,345

(22) Filed: Nov. 21, 2002

(65) Prior Publication Data

US 2003/0171663 A1 Sep. 11, 2003

Related U.S. Application Data

(63) Continuation of application No. 09/771,018, filed on Jan. 26, 2001, now abandoned, which is a continuation of application No. PCT/GB99/02516, filed on Jul. 30, 1999.

(30) Foreign Application Priority Data

| Jul. 31, 1998 | (GB) | 9816826 |
| Mar. 24, 1999 | (GB) | 9906700 |
| Apr. 23, 1999 | (GB) | 9909348 |

(51) Int. Cl.$^7$ .............................................. A61B 5/04
(52) U.S. Cl. ................. 600/391; 600/395; 600/397; 204/414; 424/443; 424/445; 424/447; 424/448
(58) Field of Search .................. 600/372, 391–395, 600/397; 424/448, 443, 445, 447; 204/414

(56) References Cited

U.S. PATENT DOCUMENTS

| 4,527,087 A | 7/1985 | Taya et al. ............... 313/487 |
| 4,539,996 A | 9/1985 | Engel ....................... 128/640 |
| 4,554,924 A | 11/1985 | Engel ....................... 128/640 |
| 4,848,353 A | 7/1989 | Engel ....................... 128/640 |
| 5,012,810 A | 5/1991 | Strand et al. ............... 128/640 |
| 5,173,302 A | 12/1992 | Holmblad et al. .......... 424/448 |
| 5,670,557 A | 9/1997 | Dietz et al. ................ 522/184 |
| 6,447,798 B1 * | 9/2002 | Munro et al. .............. 424/445 |
| 6,592,898 B2 * | 7/2003 | Munro et al. .............. 424/484 |

FOREIGN PATENT DOCUMENTS

| EP | 0012402 A1 | 6/1980 | ............. C09J/3/14 |
| EP | 0085327 A1 | 8/1983 | ............. A61B/5/04 |
| EP | 0188381 A2 | 7/1986 | ............. H01B/1/12 |
| EP | 0676457 A1 | 10/1995 | .......... C09J/133/14 |
| WO | WO93/01746 | 2/1993 | ......... A61B/5/0402 |
| WO | WO97/24149 | 7/1997 | ........... A61L/15/58 |
| WO | WO97/34947 | 9/1997 | ............ C08K/5/00 |

OTHER PUBLICATIONS

PCT International Search Report for Application No. PCT/GB99/02516 dated Dec. 7, 1999.

Search Report for British Patent Application No. GB9816826.3 dated Feb. 9, 1999.

* cited by examiner

*Primary Examiner*—Lee Cohen
(74) *Attorney, Agent, or Firm*—Palmer & Dodge LLP; Kathleen M. Williams

(57) ABSTRACT

Bioadhesive Compositions which comprise a hydrophobic polymer wherein the concentration of the polymer at the surface of the adhesive is greater than its concentration in the bulk of the adhesive are described; and biomedical electrodes, fixation products and wound dressings containing them.

12 Claims, 5 Drawing Sheets

BIOADHESIVE COMPOSITIONS AND BIOMEDICAL ELECTRODES CONTAINING THEM

RELATED APPLICATIONS

This application is a continuation application of U.S. patent application with a Ser. No. 09/771,018 filed Jan. 26, 2001 now abandond which is a conitinuation of a PCT application PCT/GB09/02516 filed Jul. 30, 1999, which claims priority to GB/9909348.6, filed Apr. 23, 1999; GB/9906700.1, filed Mar. 24, 1999; and GB/9816826.3, filed Jul. 31, 1998. The entirety of each above application is incorporated herein by reference.

This invention relates to bioadhesive compositions, particularly electrically conductive hydrogel compositions having bioadhesive properties. The invention further relates to biomedical skin electrodes incorporating such hydrogel bioadhesive compositions that are electrically conductive.

BACKGROUND

Biomedical skin electrodes are widely used in a variety of situations, whenever for example it is required to establish an electrical connection between the surface of the body of the patient and external medical equipment for transmission of electrical signals.

Modem medicine uses many medical procedures where electrical signals or currents are received from or delivered to a patient's body. The interface between medical equipment used in these procedures and the skin of the patient is usually some sort of biomedical electrode. Such electrodes typically include a conductor which must be connected electrically to the equipment, and a conductive medium adhered to or otherwise contacting skin of the patient, and they are of varying types with a wide variety of design configurations which will generally depend on their intended use and whether for example they are to be used as transmission electrodes or sensing i.e. monitoring electrodes.

Among the therapeutic procedures using biomedical electrodes are transcutaneous electric nerve stimulation (TENS) devices used for pain management; neuromuscular stimulation (NMS) used for treating conditions such as scoliosis; defibrillation electrodes to dispense electrical energy to a chest cavity of a mammalian patient to defibrillate heart beats of the patient; and dispersive electrodes to receive electrical energy dispensed into an incision made during electrosurgery.

Among diagnostic procedures using biomedical electrodes are monitors of electrical output from body functions, such as electrocardiograms (ECG) for monitoring heart activity and for diagnosing heart abnormalities.

For each diagnostic, therapeutic, or electrosurgical procedure, at least one biomedical electrode having an ionically conductive medium containing an electrolyte is adhered to or is otherwise contacted with mammalian skin at a location of interest and is also electrically connected to electrical diagnostic, therapeutic, or electrosurgical equipment. A critical component of the biomedical electrode is the conductive medium which serves as the interface between the mammalian skin and the diagnostic, therapeutic, or electrosurgical equipment, and which is usually an ionically conductive medium.

Biomedical electrodes are used among other purposes to monitor and diagnose a patient's cardiovascular activity. Diagnostic electrodes are used to monitor the patient immediately and are only applied to the patient for about five to ten minutes. Monitoring electrodes, however, are used on patients in intensive care for up to three days continuously. In contrast, Holter electrodes are used to monitor a patient during strenuous and daily activities.

Although all of the biomedical electrodes just referred to are used to record cardiovascular activity, each electrode requires specific features or characteristics to be successful. Thus, the diagnostic electrode does not have to remain adhered to a patient for extensive periods but it does have to adhere to hairy, oily, dry and wet skin effectively for the five to ten minutes of use. The monitoring electrode has to adhere for a longer period of time although the patient is often immobile during the monitoring period. The Holter electrodes is susceptible to disruption from adhesion due to physical motion, perspiration, water, etc., and therefore requires the best adhesion and at the same time comfort and electrical performance.

In the biomedical electrodes known in the prior art the ionically conductive medium which serves as an interface, between the skin of a mammalian patient and the electrical instrumentation, ranges from conductive gels and creams to conductive pressure sensitive adhesives. However, while the conductive media can be in the form of pressure sensitive conductive adhesives, for monitoring or Holter biomedical electrode use such conductive adhesives are not generally adequate on their own to maintain adhesion to mammalian skin and additional hypoallergenic and hydrophobic pressure sensitive adhesives may be employed around the conductive medium to provide the required mammalian skin adhesion. U.S. Pat. No. 5,012,810 (Strand et al.) and U.S. Pat. Nos. 4,527,087, 4,539,996, 4,554,924 and 4,848,353 (all Engel) are examples of documents that disclose biomedical electrodes which have a hydrophobic pressure sensitive adhesive surrounding the conductive medium.

In general, a desirable skin electrode is one which maintains good electrical contact with the skin and is free of localised current hot spots, i.e. exhibits uniform conductivity. For example, it has been found that a prior art electrode utilising karaya gum tends to creep in use and flatten out, exposing skin to possible direct contact with the current distribution member or lead wire. A desirable skin electrode should also usually have a low electrical impedance.

It is an object of this invention to provide hydrogel adhesives possessing controlled and predictable adhesive properties which may be readily varied to suit different uses and, in the case of medical electrodes or similar devices, different configurations or applications. It is also an object of the invention to provide such hydrogel adhesives which in addition may possess superior electrical characteristics as compared to those commonly associated with bioadhesive hydrogels.

SUMMARY OF THE INVENTION

Figure 1:
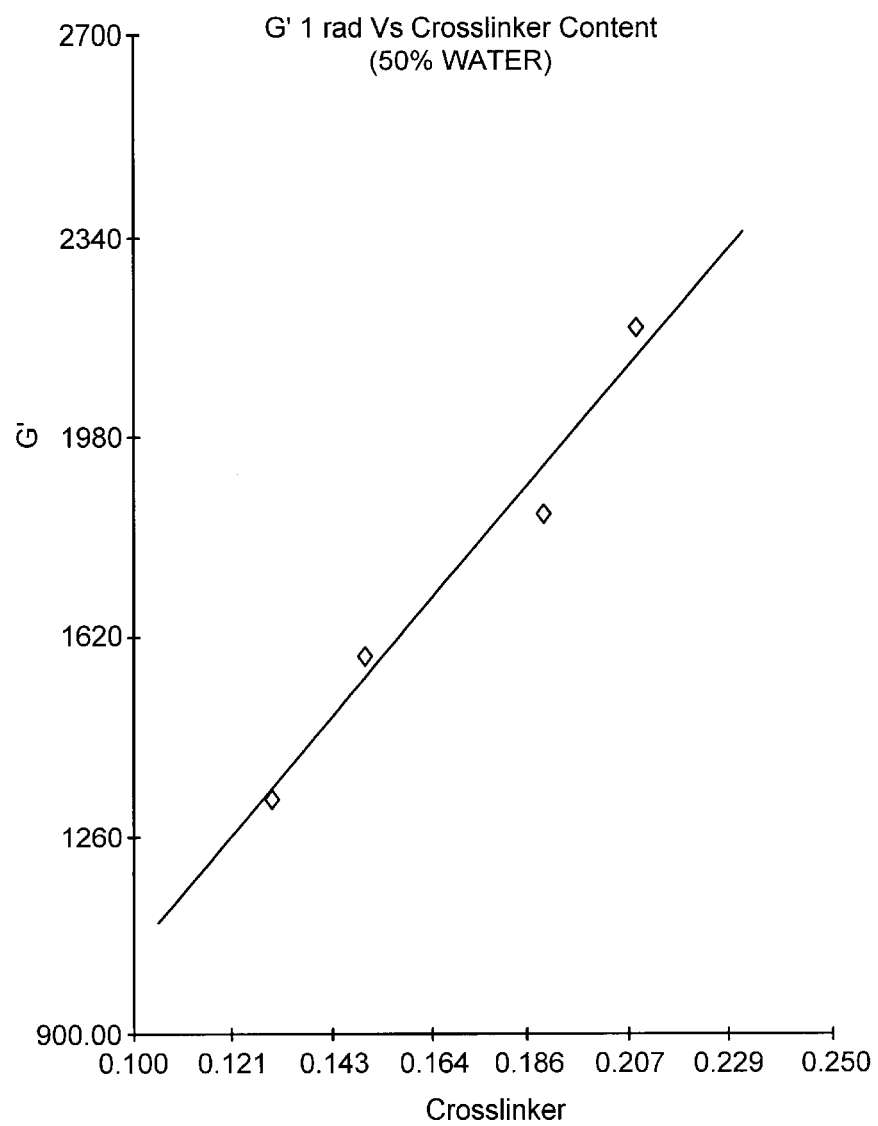
FIG. 1 is a graph showing the change in elastic modules G with respect to the amount of cross-linking agent used.

The performance of hydrogels as adhesives is related to the surface energetics of the adhesive and of the adherend (for example mammalian skin) and to the viscoelastic response of the bulk adhesive. The requirement that the adhesive wets the adherend to maximise the work of adhesion is well known. This requirement is generally met when the adhesive has a similar or lower surface energy to the adherend. The viscoelastic properties, in particular the elastic or storage modulus (G') and the viscosity modulus (G") are important. They are measured by dynamic mechanical testing at different rad/s. Their values at low rad/s (approximately 0.01 to 1 rad/s) and high rad/s (100 to 1000 rad/s) has been related to the wetting/creep behaviour and peel/quick stick properties respectively. The choice, assembly and processing of the ingredients of the hydrogel adhesive are usually targetted at making a material with a balance of properties suitable for pressure sensitive adhesive applications. A balance between the quantities and nature of polymer, plasticiser and the degree of crosslinking/entanglement has to be achieved.

The main electrical property of interest is the impedance. Performance standards have been drawn up by the American Association of Medical Instruments (AAMI). In sensing electrode applications the electrodes, consisting of the hydrogel adhesive and a suitable conductive support, are placed in pairs, adhesive to adhesive contact. The conductive support frequently has a Ag/AgCl coating in contact with the adhesive. The measured impedance is dependent on both the quality of the Ag/AgCl coating and the adhesive. In this configuration the adhesive must contain chloride ions. The concentration of chloride ions influences the impedance such that increasing the concentration can lower impedance. It would be anticipated that the activity of the ions (as opposed to the concentration) would be important in determining impedance, but in practice the determination of ion activity in these systems is not a trivial matter. It has been found that an important requirement in the control of impedance is the water content and its related activity, and in general adhesives with higher water activity have lower impedances.

When water is lost from the hydrogel both the adhesive and electrical properties are likely to change deleteriously. Whilst the presence of glycerol or other polyhydric alcohols in other reported formulations has been quoted to provide humectant properties to the hydrogel, it has been found that the most important parameter to preventing water loss is the activity of the water within the hydrogel which in turn depends on the nature and proportions of the other components and manner of processing.

Water activity in the hydrogel adhesive is primarily dependent on the water content and the nature of the polymeric components and the way in which they are processed. Water activity has been shown to have a better correlation with the growth of bacteria and moulds than water content. It has been found that organisms struggle to row at water activities less than 0.8. Enzyme activity has also been reported to decrease significantly below activity of 0.8. Water activity has also been found to influence the adhesivity of the hydrogel adhesive in that at water activities above about 0.75, they become less adhesive. A bioadhesive composition having a suitable balance of the characteristics discussed above has now surprisingly been found.

According to the invention there is provided a bioadhesive composition characterised in that it has:
(i) a water activity of from 0.4 to 0.9;
(ii) an elastic modulus at 1 rad/s of from 700 to 15,000 Pa;
(iii) an elastic modulus at 100 rad/s of from 2000 to 40,000 Pa;
(iv) a viscous modulus at 1 rad/s of from 400 to 14,000 Pa;
(v) a viscous modulus at 100 rad/s of from 1000 to 35,000 Pa;

wherein the viscous modulus is less than the elastic modulus in the frequency range of from 1 to 100 rad/s. Preferably the impedance at 500 MHz is less than 10 ohms, more preferably less than 5 ohm. When the composition includes chloride ions, the impedance at 10 Hz on Ag/AgCl electrodes is less than 1000 ohm, preferably less than 500 ohm.

Examination of the rheological properties of the compositions have been successfully used to characterise and differentiate adhesive behaviour. Typically the elastic modulus (G') and the viscous modulus (G") are measured over a range of 0.01–100 rad/s at a given temperature. For skin applications the appropriate temperature is 37° C. The moduli at low rad/s values relate to the initial bonding of the adhesive to skin and the higher to the changes in moduli values associated with de-bonding. Methods of measuring G' and G" are well known; for example a Rheometric Scientific RS-5 rheometer could be used.

The water activity of the composition can be measured using impedance methods with devices such as the Rotronic AWVC (manufactured by Rotronic). The activity of water may also be determined by placing the composition in environments of controlled humidity and temperature and measuring the changes in weight. The relative humidity (RH) at which the composition does not change weight corresponds to the activity of water in the gel (RH/100). The use of saturated salt solutions to provide the appropriate environmental conditions is well known. All compositions directly exposed to relative humidities less than that corresponding to the activity of water will be thermodynamically allowed to lose water. Exposure to greater relative humidities and the composition will gain weight.

The impedance values at 10 Hz can be measured as follows. Silver/Silver chloride electrodes are assembled from the compositions by placing 25 mm by 25 mm samples onto silver/silver chloride coated plastic eyelets (product of Micron Medical Products and marketed as plastic eyelets 107). The impedances of the compositions are recorded by contacting the electrodes face to face via the compositions and connecting to an Xtratek ET-65A ECG electrode tester (product of Xtratek of Lenexa, Kans.). The impedance at 500 MHz can be measured using an impedance meter from a 10 cm by 5 cm section of gel 0.5 cm thick placed between two conducting aluminium plates.

The bioadhesive composition preferably comprises an aqueous plasticiser, a copolymer of a hydrophilic unsaturated water-soluble first monomer and a hydrophilic unsaturated water-soluble second monomer and a cross-linking agent, the first monomer having a tendency preferentially to enhance the bioadhesive properties of the composition.

Preferably the first monomer has a tendency also to enhance the mechanical strength of the composition according to the invention and/or the second monomer has a tendency preferentially to increase the water activity of the composition. More preferably the second monomer also has a tendency preferentially to lower the electrical impedance and thereby enhance the electrical conductivity of the composition.

The bioadhesive composition is preferably obtainable by polymerising an aqueous reactive mixture comprising the said first monomer, the said second monomer and a crosslinking agent.

According to the invention there is further provided a biomedical electrode which comprises a bioadhesive composition according to the invention in association with an electrically conductive interface. The biomedical electrode optionally further comprises a support. The electrically conductive interface preferably comprises a layer of electrically conductive material which is preferably applied to the support, when present.

The invention also provides a fixation product suitable for attaching a biomedical device to skin (or the human body) e.g. a catheter, tubing, wires or cables which product comprises a bioadhesive composition according to the invention.

In preferred embodiments the first and second monomers will be acrylate based monomers selected for their ability to polymerise rapidly in water and having substantially the same molecular weight whereby in a mixture, of the two the relative proportions may be varied without significantly altering the molar characteristics of the composition.

The first monomer is preferably a compound of formula

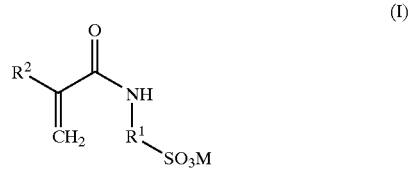

(I)

wherein $R_1$ is an optionally substituted hydrocarbon moiety, $R^2$ is hydrogen or optionally substituted methyl and ethyl, and M represents hydrogen or a cation.

$R^1$ is preferably an optionally substituted alkyl, cycloalkyl or aromatic moiety. Preferably $R^1$ represents a saturated moiety or an aromatic moiety. $R^1$ preferably contains from 3 to 12 carbon atoms, more preferably from 3 to 6 carbon atoms. A preferred moiety which $R^1$ represents is

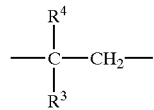

wherein $R^3$ represents hydrogen or an optionally substituted straight or branched chain alkyl group possessing from 1 to 6 carbon atoms and $R^4$ represents an optionally substituted straight or branched chain alkyl group possessing from 1 to 6 carbon atoms.

The second monomer is preferably a compound of formula

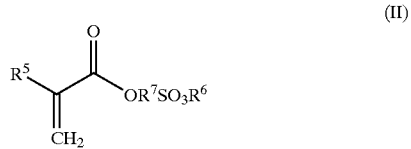

(II)

wherein $R^5$ represents hydrogen or optionally substituted methyl or ethyl, $R^6$ represents hydrogen or a cation and $R^7$ represents an optionally substituted alkyl moiety of 1 to 4 carbon atoms. Preferably $R^7$ represents optionally substituted n-propyl.

$R^1$, $R^2$, $R^3$, $R^4$, $R^5$ and $R^7$ are optionally substituted by a group which preferably has a tendency to increase the water solubility of the compound. Suitable groups will be well known to a person of skill in the art. A preferred optional substituent is a hydroxyl, amino or ammonium group or a halogen (e.g. chlorine, bromine, or iodine) atom. A suitable cation is an alkali metal cation, especially sodium or potassium.

Most preferably the first monomer is 2-acrylamido-2-methylpropanesulphonic acid or an analogue thereof or one of its salts, e.g. an alkali metal salt such as a sodium, potassium or lithium salt, while the second monomer is a polymerisable sulphonate or a salt, e.g. an alkali metal salt such as a sodium, potassium or lithium salt, of acrylic acid (3-sulphopropyl)ester or an analogue thereof. Particular preferred examples of these respective monomers are the sodium salt of 2-acrylamido-2-methylpropanesulphonic acid, commonly known as NaAMPS, and acrylic acid (3-sulphopropyl)ester potassium salt, commonly known as SPA. NaAMPS is available commercially at present from Lubrizol as either a 50% aqueous solution (reference code LZ2405) or a 58% aqueous solution (reference code LZ2405A). SPA is available commercially in the form of a solid from Raschig.

The total monomer content in the aqueous reactive mixture is preferably from 15% to 60% by weight, preferably from 20% to 50% by weight.

In preferred embodiments the ratio by weight of the first monomer to the second monomer is from 20:1 to 2:3, preferably 10:1 to 2:3; more preferably in the range 60:40 to 40:60, and may sometimes be approximately 50:50.

The first monomer is preferably included in an amount by weight of from 1% to 60%, more preferably from 5% to 50%, most preferably from 15% to 40%. The second monomer is preferably included in an amount by weight of from 1% to 50%, preferably from 10% to 30%, most preferably from 10% to 20%. The crosslinker is preferably included in an amount of from 0.01% to 2%, more preferably from 0.1 to 2% by weight. The balance of the composition preferably comprises an aqueous plasticiser.

One advantage of the first and second monomers is that it has been found that high monomer content solutions can be achieved (approximately 75%). It has also been found that the second monomer is soluble in polyhydric alcohols such as glycerol, and addition of glycerol to the first and second monomer mixture enhances the solubilisation process. It has been found that the combination of the two monomers enables a greater control over water content than can be achieved otherwise. This can be important because it has also been found that compositions made with the final water content as an integral part of the pre-gel mix have different properties from those made with an excess of water and then dried to the final composition. For example, hydrogels with a final composition obtained by the evaporation of water generally have lower elastic or storage moduli than those made with no evaporation of water. To obtain similar levels of elastic moduli, the amount of crosslinker required in the former materials is higher. The evaporation of water and extra crosslinker add to the cost of the process. This problem is avoided by the present invention where a final drying step is generally not required.

Conventional crosslinking agents are used to provide the necessary mechanical stability and to control the adhesive properties of the composition. Although compositions can be made with suitable adhesive and electrical properties, a sufficient amount of a suitable cross-linker must be used; if too little crosslinker is used, converting the material into a completed electrode becomes impossible. Typical crosslinkers include tripropylene glycol diacrylate, ethylene glycol dimethacrylate, alkoxylated triacrylate, polyethylene glycol diacrylate (PEG400 or PEG600), methylene bis acrylamide.

The aqueous reactive mixture optionally further comprises a surfactant, an additional monomer, an electrolyte, a processing aid (which is preferably a hydrophobic polymer), a water soluble polymer suitable for forming an interpenetrating polymer network, a non-hydrophilic polymer, an antimicrobial agent (e.g. citric acid, stannous chloride) and/or, for drug delivery applications, pharmaceutically active agents, the latter being designed to be delivered either passively (e.g. transdermally) or actively (e.g. iontophoretically) through the skin.

The process used to prepare bioadhesive compositions in accordance with the invention comprises mixing the ingredients to provide a reaction mixture in the form of an initial pre-gel aqueous based liquid formulation, which is then converted into a gel by a free radical polymerisation reaction. This may be achieved for example using conventional thermal initiators and/or photoinitiators or by ionizing radiation. Photoinitiation is a preferred method and will usually be applied by subjecting the pre-gel reaction mixture containing an appropriate photoinitiation agent to UV light after it has been spread or coated as a layer an siliconised release paper or other solid substrate. The processing will generally be carried out in a controlled manner involving a precise predetermined sequence of mixing and thermal treatment or history. One preferred feature of the process according to the invention is that no water is removed from the hydrogel after manufacture.

Additional Monomer

The composition according to the invention preferably comprises one or more additional monomers. A suitable additional monomer is a non-ionic monomer or ionic monomer. If the monomer is ionic, it is either anionic or cationic. Additional monomers, when present, are preferably included in an amount of up to 10% by weight.

A preferred non-ionic monomer is a N-disubstituted acrylamide (preferably an N,N-dialkylacrylamide) or an analogue thereof. N,N-dimethylacrylamide (NNDMA) and/or an analogue thereof is particularly preferred.

A preferred cationic monomer is a quaternary ammonium salt. An especially preferred cationic monomer is (3-acrylamidopropyl)trimethyl ammonium chloride or [2-(acryloyloxy)ethyl]trimethyl ammonium chloride.

A preferred anionic monomer is an acrylate based monomer such as acrylic acid or a salt or ester thereof.

Plasticiser

The compositions according to the invention generally comprise, in addition to a crosslinked polymeric network, an aqueous plasticising medium and, optionally, additional electrolyte. Plasticisers are generally used in the invention to control adhesive properties.

The aqueous plasticising medium optionally additionally comprises a polymeric or non-polymeric polyhydric alcohol (such as glycerol), an ester derived therefrom and/or a polymeric alcohol (such as polyethylene oxide). Glycerol is the preferred plasticiser. An alternative preferred plasticiser is an ester derived from boric acid and a polyhydric alcohol (such as glycerol). The aqueous reactive mixture preferably comprises from 10% to 50%, preferably from 10% to 45%, of plasticiser (other than water) by weight of the mixture.

It is well known that water in hydrogels can be present in at least two forms, freezing and non-freezing, as measured by Differential Scanning Calorimetry. In many examples of commercially available hydrogels the water is present only as non freezing water. It has been found, however, that compositions with useful adhesive properties comprising the first and second monomers can be made which have both freezing and non-freezing water, and the water activity in such gels is generally high. One advantage of including the second monomer is that it has a tendency to increase the likelihood that the compositions will contain freezing water. The advantage gained by the presence of freezing water becomes evident in the application of these gels to stress monitoring ECG. In certain cases the preferred medium for interfacing the monitoring instrument with the body is a "wet gel". It has been suggested that the advantage gained by "wet gels" is in the wetting of the skin and consequent lowering of skin impedance, but it has been found in clinical trials that hydrogels with freezing water can match the performance of "wet gels".

Electrolyte

When the compositions are intended for use in conjunction with Ag/AgCl medical electrodes, chloride ions are required to be present in order for the electrode to function. Accordingly the compositions preferably include an electrolyte except where the composition comprises an additional monomer which is a cationic monomer in the form of a chloride salt. Potassium chloride and sodium chloride are commonly used. However, any compound capable of donating chloride ions to the system may be used, for example lithium chloride, calcium chloride, ammonium chloride. The amount that should be added is dependent on the electrical properties required and is typically from 0.2 to 7% by weight. In designing the compositions for lowest impedance as measured under the AAMI standard, allowance must be given for the amount and activity of water. These factors will control the effective ion activity and hence the amount of chloride available for participating in the electrochemistry of the system. Compositions with lower chloride concentration but higher water activity have lower impedances.

Interpenetrants

The compositions preferably additionally comprise a water soluble polymer suitable for forming an interpenetrating polymer network. Hydrogels based on interpenetrating polymer networks (IPN) are well known. An IPN has been defined as a combination of two polymers, each in network form, at least one of which has been synthesised and/or crosslinked in the presence of the other. As will be appreciated, this combination will generally be a physical combination rather than a chemical combination of the two polymers. IPN systems may be described by way of example as follows:

Monomer 1 is polymerised and crosslinked to give a polymer which is then swollen with monomer 2 plus its own crosslinker and initiator.

If only one polymer in the system is crosslinked the network formed is called a semi-IPN. Although they are also known as IPN's, it is only if there is total mutual solubility that full interpenetration occurs. In most IPN's there is, therefore, some phase separation but this may be reduced by chain entanglement between the polymers. It has also been reported that semi IPN's can be made in the presence of carrier solvents (for example water in the case of hydrophilic components).

It has been found that polymerising and crosslinking water soluble monomers in the presence of water soluble polymers, water and polyhydric alcohols produces hydrogel materials with enhanced rheological and consequently adhesive properties.

Suitable water soluble polymers for the formation of semi IPN's include poly (2-acrylamido-2-methylpropanesulphonic acid) or one of its salts and its copolymers, poly (acrylic acid-(3-sulphopropyl)ester potassium salt), copolymers of NaAMPS and SPA, polyacrylic acid, polymethacrylic acid, polyethylene oxide, polyvinyl methyl ether, polyvinyl alcohol, polyvinyl-pyrrolidone, its copolymers with vinyl acetate, dimethylaminoethyl methacrylate, terpolymers with dimethylaminoethyl methacrylate and vinyl-caprolactam, polysaccharides such as gum arabic, karaya gum, xanthan gum, guar gum, carboxymethyl cellulose (CMC), NaCMC, hydroxypropylmethyl cellulose (HPMC), hydroxyethyl cellulose (HEC) or combinations thereof.

The amount of interpenetrant polymer used will be dependent on the mechanical and rheological properties required as well on consideration of processing conditions. If the interpenetrant polymer used increases the viscosity of the pre-gel mix beyond 5000 centipoise it has been found that the monomers do not polymerise and crosslink on an acceptable time scale (should be less than 60 seconds, preferably less than 10 seconds). The viscosity depends on the nature and molecular weight of the interpenetrant and the nature of pre-gel processing.

Of the natural polysaccharides, gum arabic or maltodextrin is usually preferred due to its cold water solubility and lesser effect on viscosity compared with, for example, karaya gum. A higher concentration of gum arabic than karaya may therefore be used if desired, enabling a wider control of hydrogel properties. It has also been found that the processing steps for assembling the pre-gel formulation can be critical with respect to the properties of the manufactured hydrogel. For a given formulation, if the components are assembled at 25° C. and cured different electrical and adhesive properties are obtained compared to those that have been heated to 70° C. Whilst adhesive properties may be enhanced, electrical properties e.g. low frequency impedance, can be downgraded. Solutions containing natural polysaccharides become less opaque indicative of improved solubility. The activity of water in compositions prepared from heat treated pre-gels generally is lower than in non heat treated pre-gels.

Other Additives

The composition preferably comprises a hydrophobic polymer. Hydrophobic polymers may be incorporated either in the presence or absence of interpenetrant polymers to form phase separated materials. The preparation of two phase composites consisting of a hydrophilic polymer containing an ionically conducting continuous phase and domains of a hydrophobic pressure sensitive adhesive which enhance adhesion to mammalian skin have been reported in U.S. Pat. No. 5,338,490. The method of preparation described therein involved casting a mixture (as a solution and or suspension) consisting of the hydrophilic polymer containing phase and hydrophobic components onto a substrate and then removing the solvent. It has been found, however, that adhesive ionically conducting hydrogels may be better prepared by combining the hydrophobic polymer (preferably as an emulsion) with the components of the pre-gel reaction mixture and casting these onto a substrate and curing. In other words, there is no need to remove a solvent in order to form useful materials. Furthermore, the hydrophilic phase of the composition in addition to being a crosslinked network may also be an IPN or semi IPN.

It is believed that when hydrophobic polymers are incorporated in this way that the hydrophobic component segregates to the surface (as determined by Fourier transform infrared attenuated total reflectance spectroscopy, FTIR ATR, approximate sampling depth 1 $\mu$m using a ZnSe crystal or 0.25 $\mu$m with a Germanium crystal) and that it is the amount of the hydrophobic component present in the surface that influences the adhesion to a wide variety of materials. The greater the amount of the hydrophobic component in the surface the greater the adhesion. In U.S. Pat. No. 5,338,490 weight ratios of the hydrophilic phase to the hydrophobic phase of 60:1 to 8:1 were claimed. In hydrogel adhesives of between 100 to 2000 microns thick made in accordance with the present invention, ratios of hydrophobic to hydrophobic components ranging from 7:1 to 1:20 have been found to be preferable, especially when these ratios are present in the surface of the adhesive composition. In the process of the present invention, however, it may take up to 72 hours from the initial curing of the adhesive hydrogel for the segregation of the hydrophobic materials to the surface, as defined by the ATR sampling depth, to be complete.

Preferably, the hydrophobic pressure sensitive adhesive in such embodiments is selected from the group consisting of polyacrylates, polyolefins, silicone adhesives, natural or synthetically derived rubber base and polyvinyl ethers or blends thereof. Preferably the hydrophobic pressure sensitive adhesive in these embodiments is an ethylene/vinyl acetate copolymer such as that designated DM137 available from Harlow Chemicals or vinyl acetate dioctyl maleate such as that designated Flexbond 150 and sold by Air Products. Those skilled in the art will also know that the molecular weight and comonomer ratios may be altered to control the properties of hydrophobic pressure sensitive adhesives. In general, the degree of surface segregation exhibited by such hydrophobic pressure sensitive adhesive (HPSA) will be dependent on factors such as composition of the HPSA, viscosity of the pre-gel mixture, temperature and rate of curing.

The bioadhesive composition according to the invention preferably is such that the relative amount of hydrophobic polymer (which is the amount of hydrophobic polymer relative to the amount of monomer) is preferably at least four times greater, more preferably at least eight times greater, at the surface of the composition compared to what it is in the bulk of the composition. The relative amount at the surface is preferably the relative amount in the composition at a depth of up to 1 micron (as measured using FTIR ATR using a ZnSe crystal), preferably up to 0.25 micron (as measured using FTIR ATR using a Germanium crystal). The relative amount is measured by obtaining the ratio of the peak height of the peak in the carbonyl region for the hydrophobic polymer to the peak height of the peak in the carbonyl region for the first monomer, using the relevant FTIR ATR technique. The wave number values for the relevant peaks for the hydrophobic polymer and the monomer are well known.

More preferably, the ratio of the relative amount in the surface of the composition at a depth of up 0.25 micron to the relative amount in the surface of the composition at a depth of up 1 micron is more than 1:1, more preferably more than 1.25:1, most preferably more than 1.5:1.

Surfactant

The composition according to the invention optionally includes a surfactant.

Any compatible surfactant may be used. Nonionic, anionic and cationic surfactants are preferred, either alone or in combination. The surfactant is preferably included in an amount from 0.1% to 20% by weight, more preferably 0.1% to 10% by weight.

The bioadhesive compositions according to the invention are also useful in a variety of consumer care applications. For example they can be used as the adhesive for a faecal management device, wound dressing or prosthesis, e.g. hair prosthesis.

The addition of citric acid is also of interest since it also has the capacity to decrease the electrical impedance as hereinafter described in connection with EXAMPLE 4.

The invention will be further described with reference to the graphs of FIGS. 1 to 5 of the accompanying drawings and the following Examples in connection with bioadhesive compositions suitable for use in medical skin electrodes or in fixation products.

EXAMPLE 1

In 20 parts of polyethylene glycol diacrylate (pEG600) (product of UCB Chemicals marketed under the trade name designation of Ebacryl 11) were dissolved 6 parts of 1-hydroxycyclohexyl phenyl ketone (product of Ciba and marketed under the trade name designation of Irgacure 184). The solution so produced is herein designated solution A (XL/PI). Separately, 50 parts of the potassium salt of 3-sulphopropyl acrylate (SPA) (product of Raschig) were dissolved in 50 parts water to form solution B. A further solution designated solution C consisted of 50 parts water, 50 parts of the sodium salt of 2-acrylamido-2-methylpropane sulphonic acid (NaAMPS) product of the Lubrizol Corporation and marketed as a 50% aqueous solution under the trade name LZ2405). Mixtures of solutions B and C in the ratios of 100:0, 90:10, 60:40, 50:50, 40:60, 10:90 and 0:100 were made to form pre-gel solutions. To 80 parts of each of these pre-gel solutions, 0.15 parts of solution A, 5 parts potassium chloride and 20 parts distilled water were added. The pre-gel solutions were coated onto siliconised release paper at a coat weight of 0.8 kilograms per square meter and exposed to ultraviolet radiation by being passed under a medium pressure mercury arc lamp at a speed of 5 meters per minute to form clear self supporting gels. The residence time under the lamp was 4 seconds. The storage moduli(G') of 20 mm diameter discs stamped from the gels were recorded on a Rheometric Scientific RS-5 rheometer at 37° C. The G' values at 1 rad are recorded in Table 1. Silver/Silver chloride electrodes were assembled from the gels by placing 25 mm by 25 mm samples onto silver/silver chloride coated plastic eyelets (product of Micron Medical Products and marketed as plastic eyelets 107). The impedances of the gels were recorded by contacting the gelled electrodes face to face via the gels and connecting to an Xtratek ET-65A ECG electrode tester (product of Xtratek of Lenexa, Kans.). The impedance data are recorded in Table 1. The percentage of freezing water present in the gels, also recorded in Table 1, were obtained by cooling small weighed samples of gel (ca. 2 mg) in sealed aluminium pans to −70° C. and heating at 10° C. per minute in a Perkin Elmer differential scanning calorimeter, DSC2. Using a calibration graph produced from samples of pure water, the area under the observed endotherm peaks was converted to the weight of freezing water in the sample. With the exception of the gels containing 90 and 100 parts SPA, the gels produced had acceptable tack and peel properties on the skin. From the data in Table 1 relatively linear changes in storage modulus and freezing water content are obtained on increasing or decreasing the SPA to NaAMPS ratio. The changes in impedance are small but surprisingly appear to be non linear.

In the above Example, and in the following Examples wherever parts are mentioned they are meant as parts by weight unless otherwise specified.

TABLE 1

| | | | | | | | |
|---|---|---|---|---|---|---|---|
| NaAMPS SolutionC | 80 | 72 | 48 | 40 | 32 | 8 | 0 |
| SPA SolutionB | 0 | 8 | 32 | 40 | 48 | 72 | 80 |
| Distilled Water | 20 | 20 | 20 | 20 | 20 | 20 | 20 |
| XL/PI SolutionA | 0.15 | 0.15 | 0.15 | 0.15 | 0.15 | 0.15 | 0.15 |
| KCl | 5 | 5 | 5 | 5 | 5 | 5 | 5 |
| G'(Pa) @ 1 rad/s | 4,198 | 3,389 | 2,471 | 2,205 | 1,759 | 703 | 492 |
| Impedance (Ohms) | 44 | 43 | 41 | 41 | 39 | 38 | 38 |
| % Freezing Water | 20 | 24 | 30 | 34 | 35 | 41 | 44 |

EXAMPLE 2

In 20 parts of polyethylene glycol diacrylate (pEG600) (product of UCB Chemicals marketed under the trade name designation of Ebacryl 11) 6 parts of 1-hydroxycyclohexyl phenyl ketone (product of Ciba and marketed under the trade name designation of Irgacure 184) were dissolved. (This solution is designated solution A) (XL/PI). Separately 58 parts of the potassium salt of 3-sulphoproylacrylate (SPA) (product of Raschig) were dissolved in 58 parts distilled water to form solution D. A further solution designated solution E consisted of 42 parts water, 58 parts of the sodium salt of 2-acrylamido-2-methylpropane sulphonic acid (NaAMPS) (a product of the Lubrizol Corporation marketed as a 58% aqueous solution under the trade name LZ2405A). Mixtures of solutions D and E in the ratios 100:0, 90:10, 60:40, 50:50, 40:60, 10:90 and 0:100 were made to form pre-gel solutions. To 100 parts of each of these pre-gel solutions, 0.17 parts of solution A and 3 parts potassium chloride were added. The pre-gel solutions were coated onto siliconised release paper at a coat weight of 0.8 kilograms per square meter and passed under a medium pressure mercury arc lamp at a speed of 5 meters per minute to form clear self-supporting gels. Storage moduli, impedances and % freezing water were measured as in Example 1 and are recorded in Table 2. As in the gels described in Example 1 the changes in the elastic or storage modulus G'(Pa) are linear with respect to the increasing or decreasing ratio of NaAMPS to SPA. However, surprisingly both the impedance and % freezing water content exhibit distinct non-linear behaviour. All the gels produced possess acceptable tack and peel strength against skin. The gels with NaAMPS:SPA ratios in the range of 60:40 to 40:60, however, have a better balance of reusability and peel strength.

TABLE 2

| NaAMPS SolutionE | 100 | 90 | 60 | 50 | 40 | 10 | 0 |
|---|---|---|---|---|---|---|---|
| SPA SolutionD | 0 | 10 | 40 | 50 | 60 | 90 | 100 |
| XL/PI SolutionA | 0.17 | 0.17 | 0.17 | 0.17 | 0.17 | 0.17 | 0.17 |
| KCl | 3 | 3 | 3 | 3 | 3 | 3 | 3 |
| G'(Pa) @ 1 rad/s | 15,142 | 14,333 | 11,073 | 10,672 | 9,920 | 6,280 | 5,199 |
| Impedance (Ohms) | 62 | 61 | 49 | 46 | 43 | 40 | 40 |
| % Freezing Water | 0 | 0 | 0.5 | 1 | 1.8 | 23 | 25 |

Upon varying the amount of the cross-linking agent a substantially linear change in the elastic modulus G' can also be obtained, as illustrated by the graph of FIG. 1.

EXAMPLE 3

To 57 parts of a 58% solution of the sodium salt of 2-acrylamido-2-methylpropane sulphonic acid (NaAMPS) (LZ2405A) 10 parts of a 58% solution of the potassium salt of 3-sulphopropyl acrylate (SPA) were added along with 5 parts potassium chloride and stirred until the potassium chloride has dissolved. This solution was then mixed with 30 parts glycerol for 30 minutes. To the latter solution were added 0.15 parts of a solution containing 20 parts of polyethylene glycol diacrylate (pEG600) (product of UCB Chemicals marketed under the trade name designation of Ebacryl 11) in which 6 parts of 1-hydroxycyclohexyl phenyl ketone (product of Ciba and marketed under the trade name designation of Irgacure 184) were dissolved. The so-formed pre-gel solution was then cured as in Example 1. The impedance of the resulting gel, measured as described in Example 1, was 83 Ohms. Good skin adhesion properties were obtained for this gel. The impedance of a similar gel made from 67 parts of a 58% solution of the sodium salt of 2-acrylamido-2-methylpropane sulphonic acid but with no SPA had an impedance of 105 Ohms. This demonstrates that the presence of SPA gives rise to a reduction in impedance.

EXAMPLE 4

The method of Example 3 was repeated with 1 part citric acid being added with the potassium chloride. The impedance of a similar gel (denoted 4B in Table 3) made from 67 parts of a 58% solution of the sodium salt of 2-acrylamido-2-methylpropane sulphonic acid but no SPA had an impedance of 96 Ohms demonstrating again that the addition of SPA reduces the impedance. From the data summarised in TABLE 3, however, it is seen that addition of citric acid also gives rise to a reduction in impedance, and the effect is surprisingly large for a gel with SPA and NaAMPS. The adhesion to skin and reusability characteristics for this gel of Example 4 containing citric acid and SPA were better than the gel described in Example 3.

TABLE 3

| Example | 3A | 3B | 4A | 4B |
|---|---|---|---|---|
| NaAMPS (58% soln) | 67 | 57 | 67 | 57 |
| SPA (58% soln) | 0 | 10 | 0 | 10 |
| Glycerol | 30 | 30 | 30 | 30 |
| Citric Acid | 0 | 0 | 1 | 1 |
| Crosslinker/ Photoinitiator | 0.15 | 0.15 | 0.15 | 0.15 |
| Impedance (ohms) | 105 | 85 | 96 | 61 |

EXAMPLE 5

The formulations listed in Table 4 were prepared using the following method which is for formulation 5a. To 58 parts of a 50% aqueous solution of the sodium salt of 2-acrylamido-2-methylpropane sulphonic acid (NaAMPS) (LZ2405) 2 parts of the potassium salt of 3-sulphopropyl acrylate (SPA) were added along with 1.575 parts of acrylic acid and stirred. This solution was then mixed with 37 parts glycerol for 30 minutes. To the latter solution were added 0.175 parts of solution (F). Solution F contains 20 parts of an alkoxylated triacrylate (product of UCB Chemicals marketed under the trade name designation of IRR 210) in which 1.4 parts of 1-hydroxycyclohexyl phenyl ketone (product of Ciba and marketed under the trade name designation of Irgacure 184) are dissolved. The so-formed pre-gel solution was then cured as in Example 1. The G' and G" moduli were measured from 20 mm diameter discs of the gel using a Rheometric Scientific RS-5 rheometer at 37° C.

To prepare formulation 5b, the same method was repeated except that 0.15 parts of solution F were used instead of 0.175 parts.

To prepare formulations 5c and 5d, the same method used for formulation 5a was repeated except that the parts by weight were changed to the figures given in Table 4A. The potassium chloride was added instead of the acrylic acid; for formulation 5d, deionised water was also added.

TABLE 4

| | Composition in parts by weight | | | |
|---|---|---|---|---|
| Formulation | 5a | 5b | 5c | 5d |
| 50% NaAMPS | 58 | 58 | 75 | 75 |
| KCl | | | 5 | 5 |
| Acrylic Acid | 1.575 | 1.575 | | |
| SPA | 2 | 2 | 2 | 2 |
| Glycerol | 37 | 37 | 25 | 25 |
| DI WATER | | | | 3 |

TABLE 4-continued

| | Composition in parts by weight | | | |
|---|---|---|---|---|
| Formulation | 5a | 5b | 5c | 5d |
| PI/XL (Solution) | 0.175(F) | 0.15(F) | 0.15(A) | 0.15(A) |
| G'(Pa), @ 1 rad/s | 1455 | | 1054 | |
| G'Pa) @ 100 rad/s | 5174 | | 4613 | |
| G"(Pa) @ 1 rad/s | 601 | | 488 | |
| G"(Pa) @ 100 rad/s | 2906 | | 2640 | |

EXAMPLE 6

The formulations listed in Table 5 were prepared using the following method which is for formulation 6a. To 67 parts of a 58% aqueous solution of the sodium salt of 2-acrylamido-2-methylpropane sulphonic acid (NaAMPS) (LZ2405A) 2 parts of the potassium salt of 3-sulphopropyl acrylate (SPA) were added along with 5 parts of potassium chloride and 1 part of citric acid and stirred until the potassium chloride had dissolved. This solution was then mixed with 30 parts glycerol for 30 minutes. To the latter solution were added 0.13 parts of solution A prepared as described in Example 1. The so-formed pre-gel solution was then cured as in Example 1. The G' and G" moduli were measured from 20 mm diameter discs of the gel using a Rheometric Scientific RS-5 rheometer at 37° C.

To prepare formulation 6b, the same method was repeated except that the potassium chloride and citric acid were omitted, 0.06 parts by weight of solution G were used instead of solution A and the amounts of the other ingredients were changed to the amounts given in Table 5. Solution G contains 20 parts of polyethylene glycol diacrylate (molecular weight 400) (product of UCB Chemicals marketed under the trade name designation of IRR 280) in which 6 parts of 1-hydroxycyclohexyl phenyl ketone (product of Ciba and marketed under the trade name designation of Irgacure 184) are dissolved.

To prepare formulations 6c and 6d, the same method used for formulation 6a was repeated except that citric acid was omitted, 0.06 parts of solution G were used instead of solution A and the parts by weight were changed to the figures given in Table 5.

To prepare formulation 6e, the same method used for formulation 6a was repeated except that gum arabic and the ethylene/vinyl acetate copolymer designated DM137 and sold by Harlow Chemicals were added instead of citric acid and the parts by weight were changed to the figures given in Table 5.

To prepare formulation 6f, the same method used for formulation 6a was repeated except that the ethylene/vinyl acetate copolymer designated DM137 and sold by Harlow Chemicals, polyethylene glycol (molecular weight 400) and sodium nitrate were added with the citric acid and the parts by weight were changed to the figures given in Table 5.

TABLE 5

| | Composition in parts by weight | | | | | |
|---|---|---|---|---|---|---|
| Formulation | 6a | 6b | 6c | 6d | 6e | 6f |
| 58% NaAMPS | 67 | 57 | 57 | 57 | 67 | 50 |
| KCl | 5 | | 5 | 5 | 5 | 1 |
| Citric Acid | 1 | | | | | 1 |
| SPA | 2 | 10 | 10 | 10 | 2 | 18 |
| Glycerol | 30 | 33 | 33 | 28 | 30 | 20 |
| Gum Arabic | | | | | 2 | |
| DM 137 | | | | | 2 | 3 |
| PEG 400 | | | | | | 10 |
| Sodium Nitrate | | | | | | 0.05 |
| PI/XL (Solution) | 0.13(A) | 0.06(G) | 0.06(G) | 0.075(G) | 0.25(A) | 0.175(A) |
| G'(Pa) @ 1 rad/s | 2973 | 4326 | | 3019 | 4637 | |
| G'(Pa) @ 100 rad/s | 9800 | 13986 | | 9763 | 8789 | |
| G"(Pa) @ 1 rad/s | 1265 | 1914 | | 1200 | 1029 | |
| G"(Pa) @ 100 rad/s | 4597 | 6707 | | 4537 | 3952 | |

EXAMPLE 7

To 34.7 parts of a 58% aqueous solution of the sodium salt of 2-acrylamido-2-methylpropane sulphonic acid (NaAMPS) (LZ2405A) 34.7 parts of a 58% aqueous solution of the potassium salt of 3-sulphoproyl acrylate (SPA) were added along with 4.6 parts potassium chloride and 3 parts distilled water and stirred until the potassium chloride has dissolved. This solution was then mixed with 23.2 parts glycerol for 30 minutes. To the latter solution were added 0.15 parts of solution A prepared as described in Example 1. The so-formed pre-gel solution was then cured as in Example 1. The impedance of the resulting gel as measured as described in Example 1 was 48 Ohms. In vivo tests on the thigh skin of a Caucasian male using a frequency response analyser (Solartron 1172) and skin impedance analyser in a three electrode configuration (test, control and reference) indicated that this gel has the electrical characteristics of commercially available wet gels despite having the mechanical characteristic associated with most commercially available hydrogel adhesives.

EXAMPLE 8

To 20 parts glycerol, 3 parts of a hydrophobic ethylene/vinyl acetate copolymer emulsion (50% solids) (product of Harlow Chemicals marketed under the trade name DM137) and 10 parts polyethylene glycol (molecular weight 600) were added and stirred until a uniform colour was obtained. To this mixture were added 50 parts of a 58% solution of the sodium salt of 2-acrylamido-2-methylpropane sulphonic acid (NaAMPS) (LZ2405A), 16 parts potassium salt of 3-sulphopropyl acrylate (SPA) and 5 parts potassium chloride, and the solution was heated with stirring to 60° C. for one hour. The mixture had changed from an opaque off white to a translucent off white appearance. The turbidity of the solutions as measured in a portable turbidity meter, product code H193703 marketed by Hanna had changed from 254 ftu to 107 ftu. The solution was cooled to 20° C. and then there was added 0.13 parts of solution A prepared as described in Example 1. This final solution was stirred for one hour and then cured as in Example 1. The resulting gel had an impedance of 254 Ohms and a G' value at 1 rad of 5328 Pa. The activity of water in the gel, as determined by placing the gel into cabinets at varying levels of humidity at 40° C. (40, 52, 64 and 80% RH) and measuring weight uptake or loss and extrapolating to zero weight change, was 0.62. The adhesion to skin of this gel was significantly greater than those described in the previous examples. Analysis of the gel by attenuated total reflectance infra-red spectroscopy revealed that in the surface regions (about 1 micron or less), either the air surface or the surface in contact with the release paper, the concentration of the ethylene/vinyl acetate copolymer relative to the NaAMPS was significantly enhanced compared to the bulk composition.

EXAMPLE 9

The method of Example 8 was carried out except that with the glycerol were added 3 parts of gum arabic. The resulting gel had an impedance of 358 Ohms and a G' value at 1 rad of 5406 Pa. The activity of water as determined by the method in Example 8 was 0.55. The adhesion to skin of this gel was significantly greater than those described in the previous examples. Analysis of the gel by attenuated total reflectance infra-red spectroscopy revealed that in the surface region (about 1 micron or less), either the air surface or the surface in contact with the release paper, the concentration of the ethylene/vinyl acetate copolymer relative to the NaAMPS was significantly enhanced compared to the bulk composition.

EXAMPLE 10

The formulations shown in Tables 6 and 7 were prepared using the following method which is for formulation 10a. To 20 parts glycerol, 15 parts of a hydrophobic vinyl acetate/dioctyl maleate copolymer emulsion (product of Air Products marketed under the trade name Flexbond 150) were added and stirred until a uniform colour was obtained. To this mixture were added 44 parts of a 58% solution of the sodium salt of 2-acrylamido-2-methylpropane sulphonic acid (NaAMPS) (LZ2405A), 20 parts potassium salt of 3-sulphopropyl acrylate (SPA) and 4 parts potassium chloride, and the solution was heated with stirring to 60° C. for one hour. The solution was cooled to 20° C. and then there was added 0.13 parts of solution G prepared as described in Example 6. This final solution was stirred for one hour and then cured as in Example 1. The G' and G" moduli were measured from 20 mm diameter discs of the gel using a Rheometric Scientific RS-5 rheometer at 37° C.

Figure 2:
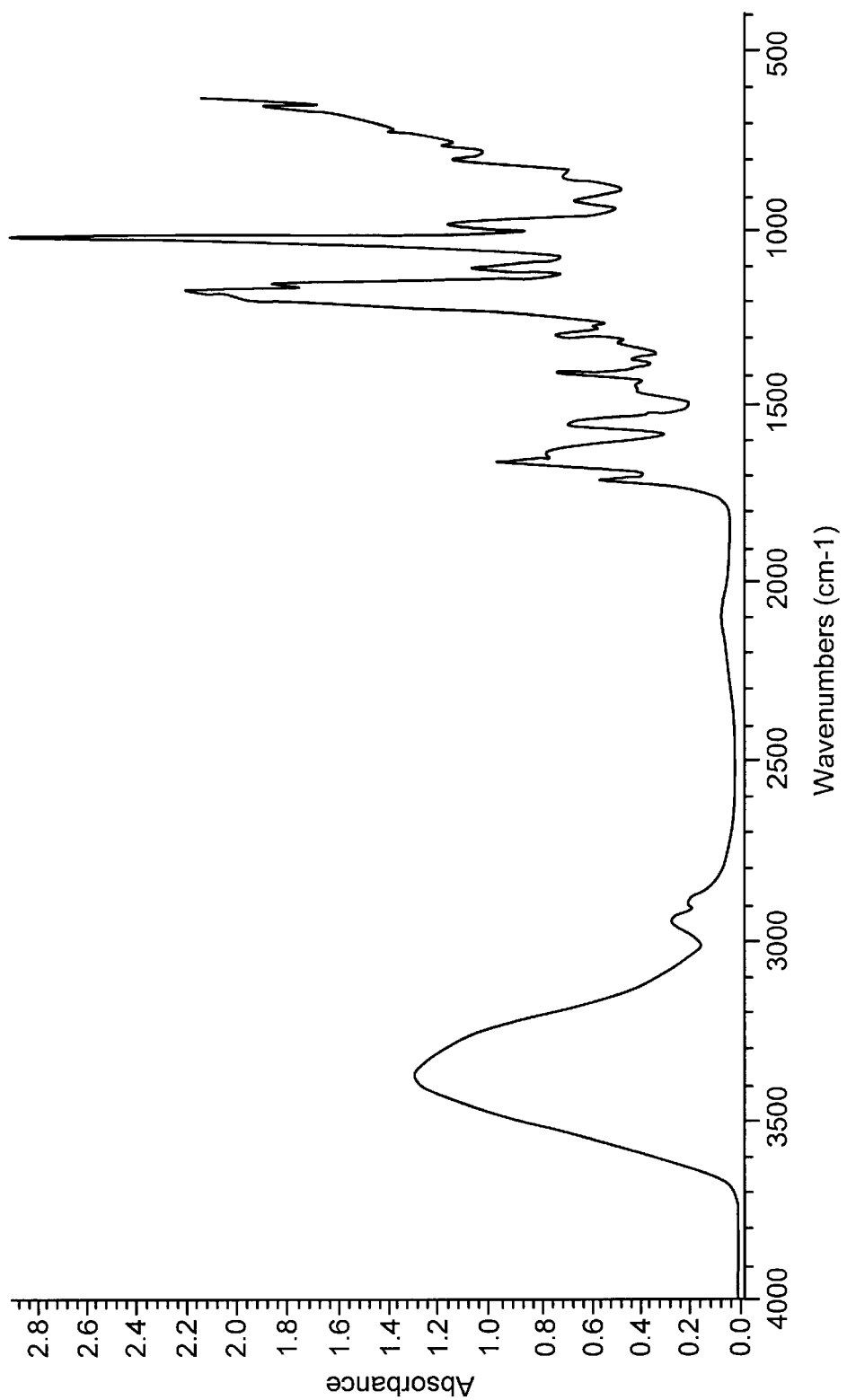
FIGS. 2–5 show fourier transform reflectance spectra graphs for different mixtures of the bioadhesive compositions.
Figure 3:
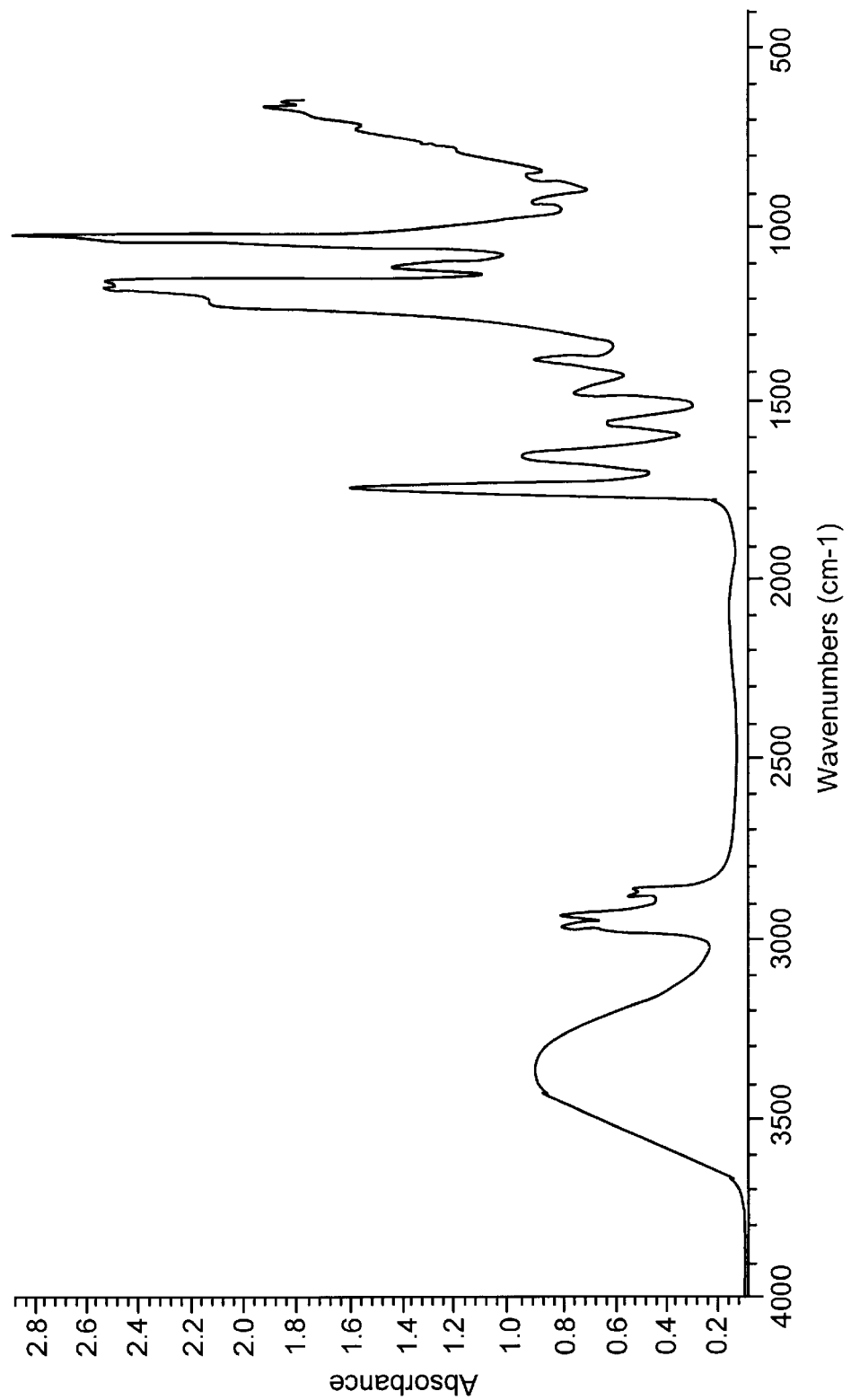

Fourier transform infrared attenuated total reflectance spectra (FTIR ATR) were taken of both the pregel mixture and of the gel formed after polymerisation using a ZnSe crystal (approximate sampling depth 1 $\mu$m). The results obtained are shown in FIGS. 2 and 3, respectively. The peak at around 1740 cm$^{-1}$ corresponds to the hydrophobic polymer whereas the peak at around 1550 cm$^{-1}$ corresponds to NaAMPS. It can be seen that before polymerisation the ratio in height of the former peak to the latter peak is about 0.25:1 whereas after polymerisation, the ratio is about 2.9:1. This shows a twelve-fold increase in the concentration of the hydrophobic polymer at the surface of the gel after polymerisation indicating that the hydrophobic polymer surface segregates. A further FTIR ATR spectrum was taken of the gel formed after polymerisation using a germanium crystal (approximate sampling depth 0.25 $\mu$m). It was found that the ratio in the height of the former peak to the latter peak is 3.9:1 showing a sixteen fold increase in the concentration of the hydrophobic polymer on the surface of the gel.

To prepare formulation 10b, the same method used for formulation 10a was repeated except that a hydrophobic ethylene/vinyl acetate copolymer emulsion (50% solids) (product of Harlow Chemicals marketed under the trade name DM137) was used instead of Flexbond 150, 3 parts polyethylene glycol (molecular weight 600) were added with the hydrophobic copolymer DM137 and the parts by weight were changed to the figures given in Table 6.

Figure 4:
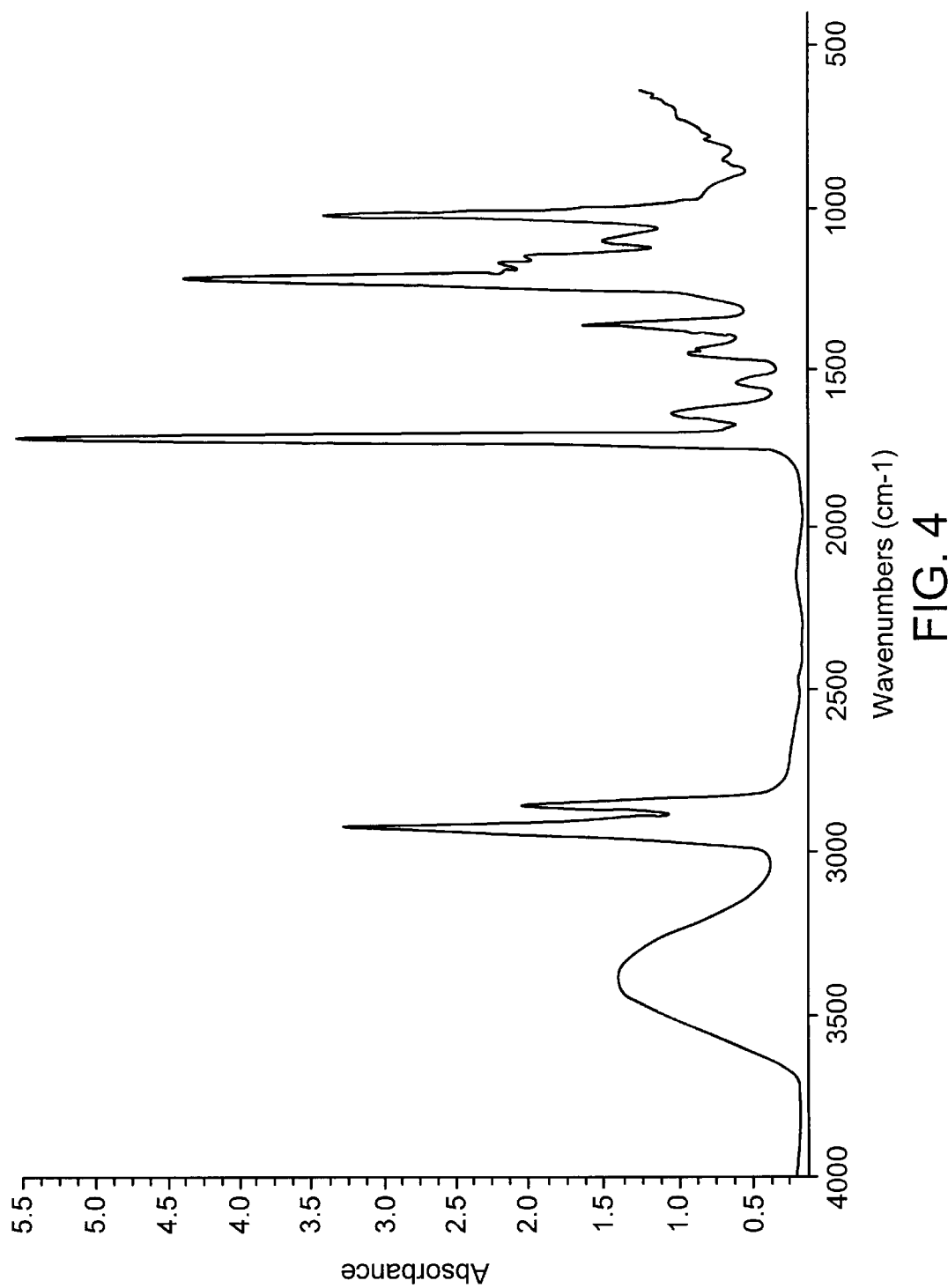
Figure 5:
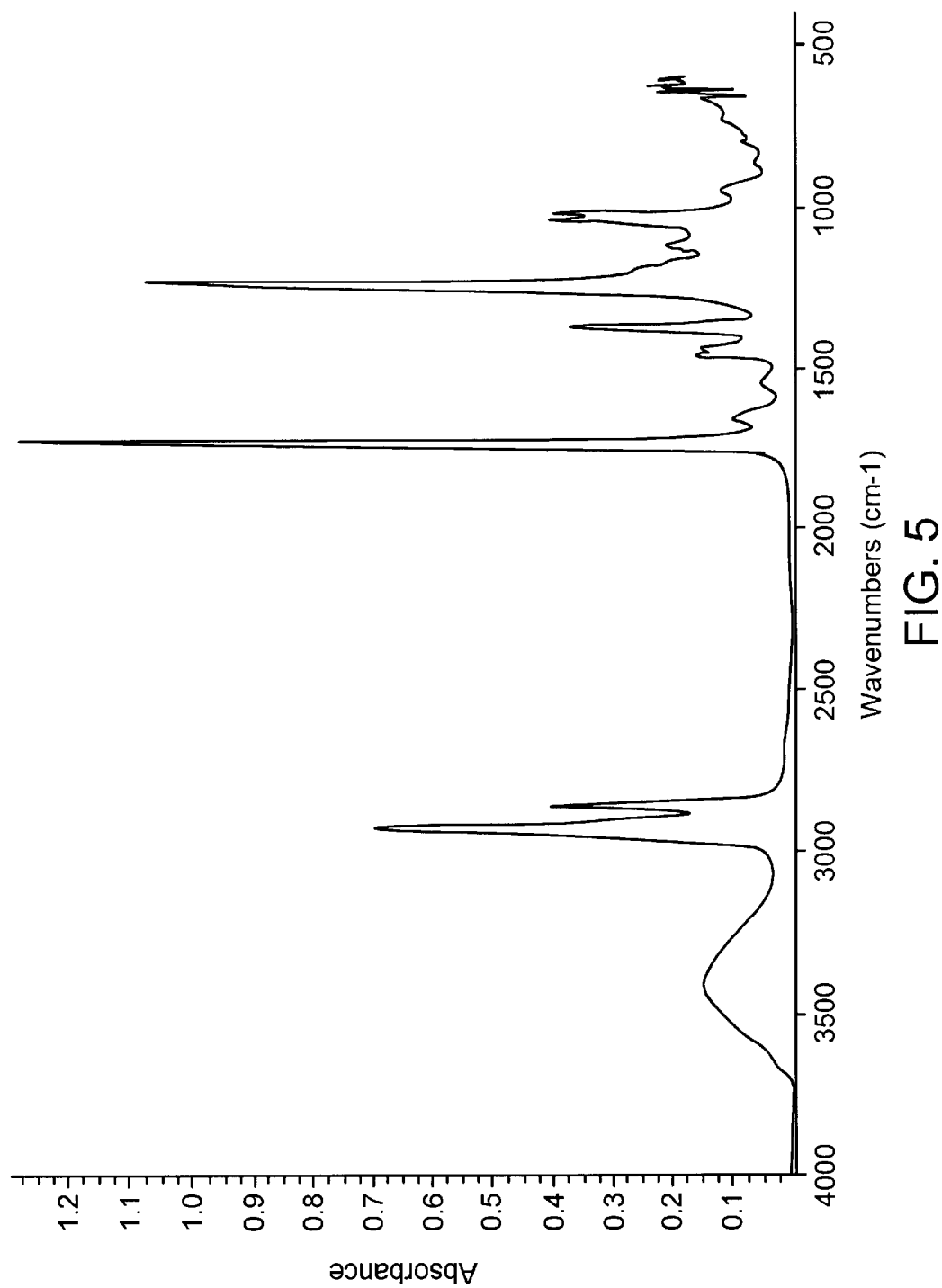

FTIR ATR were taken of the gel formed after polymerisation using a ZnSe crystal (approximate sampling depth 1 $\mu$m) and a germanium crystal (approximate sampling depth 0.25 $\mu$m). The results obtained are shown in FIGS. 4 and 5, respectively. As for formulation 10a, the peak at around 1740 cm$^{-1}$ corresponds to the hydrophobic polymer whereas the peak at around 1550 cm$^{-1}$ corresponds to NaAMPS. The ratio of the former peak to the latter peak for FIG. 4 (the ZnSe FTIR ATR spectrum) is about 21:1 whereas the ratio for FIG. 5 (the germanium FTIR ATR spectrum) is about 11:1. This again demonstrates the hydrophobic polymer segregates to the surface of the gel.

To prepare formulation 10c, the same method used for formulation 10a was repeated except that a hydrophobic ethylene/vinyl acetate copolymer emulsion (50% solids) (product of Harlow Chemicals marketed under the trade name DM137) was used instead of Flexbond 150, 0.05 parts of sodium nitrate were added with the potassium chloride and the parts by weight were changed to the figures given in Table 6.

To prepare formulations 10d and 10e, the same method used for formulation 10b was repeated except that solution A as described in Example 1 was used instead of solution G and the parts by weight were changed to the figures given in Table 6.

To prepare formulations 10f and 10g, the same method used for formulation 10d was repeated except that potassium chloride was omitted and the parts by weight were changed to the figures given in Table 6.

TABLE 6

| Formulation | 10a | 10b | 10c | 10d | 10e | 10f | 10g |
|---|---|---|---|---|---|---|---|
| COMPOSITION by WEIGHT | | | | | | | |
| 58% NaAMPS | 44 | 44 | 65 | 35 | 35 | 35 | 37 |
| KCl | 4 | 5 | 5 | 5 | 5 | | |
| SPA | 20 | 20 | 10 | 25 | 25 | 15 | 18 |
| Glycerol | 20 | 20 | 23 | 20 | 20 | 30 | 30 |
| Gum Arabic | | | | | | | |
| DM 137 | | 15 | 2 | 15 | 15 | 15 | 10 |
| Flexbond 150 | 15 | | | | | | |
| PEG 600 | | 3 | | 10 | 10 | 5 | 5 |
| Sodium Nitrate | | | 0.05 | | | | |
| PI/XL | 0.13 | 0.13 | 0.15 | 0.12 | 0.13 | 0.15 | 0.15 |
| (Solution) | (G) | (G) | (G) | (A) | (A) | (A) | (A) |
| G'(@ 1 rad/s) | 6156 | 4756 | | | | | |
| G'(@ 100 rad/s) | 15219 | 15412 | | | | | |
| G"(@ 1 rad/s) | 1775 | 1840 | | | | | |
| G"(@ 100 rad/s) | 5748 | 7743 | | | | | |

To prepare formulations 10h, 10i and 10j, the same method used for formulation 10g was repeated except that the parts by weight were changed to the figures given in Table 7.

To prepare formulations 10k, 10l and 10m, the same method used for formulation 10j was repeated except that a propylene oxide/ethylene oxide block copolymer surfactant (designated PE/F127 and manufactured by BASF) was added with the glycerol and the parts by weight were changed to the figures given in Table 7.

TABLE 7

| Formulation | 10h | 10i | 10j | 10k | 10l | 10m |
|---|---|---|---|---|---|---|
| COMPOSITION by WEIGHT | | | | | | |
| 58% NaAMPS | 37 | 35 | 35 | 35 | 35 | 35 |
| SPA | 18 | 15 | 25 | 25 | 25 | 25 |
| Glycerol | 30 | 33 | 20 | 20 | 20 | 20 |
| DM 137 | 10 | 10 | 15 | 15 | 15 | 15 |
| PEG 600 | 10 | 5 | 10 | 10 | 10 | 10 |
| PE/F127 | | | | 1 | 5 | 9 |
| PI/XL (Solution) | 0.15(A) | 0.15(A) | 0.14(A) | 0.14(A) | 0.14(A) | 0.14(A) |

As will be seen, the invention presents a number of different aspects and it should be understood that it embraces within its scope all novel and inventive features and aspects herein disclosed, either explicitly or implicitly and either singly or in combination with one another. Also, many detail modifications are possible and, in particular, the scope of the invention is not to be construed as being limited by the illustrative example(s) or by the terms and expressions used herein merely in a descriptive or explanatory sense.

What is claimed is:

1. A bioadhesive composition comprising:
   (i) a water activity in the range of 0.4 to 0.9;
   (ii) an elastic modulus at 1 rad/s in the range of 700 to 15,000 Pa;
   (iii) an elastic modulus at 100 rad/s in the range of 2000 to 40,000 Pa;
   (iv) a viscous modulus at 1 rad/s in the range of 400 to 14,000 Pa; and
   (v) a viscous modulus at 100 rad/s in the range of 1000 to 35,000 Pa;
   wherein the viscous modulus is less than the elastic modulus in a frequency range of 1 to 100 rad/s, and wherein the impedance of said composition at 500 MHz is less than 10 ohms.

2. A bioadhesive composition according to claim 1 which comprises an aqueous plasticiser, a copolymer of a hydrophilic unsaturated water-soluble first monomer, a hydrophilic unsaturated water-soluble second monomer, and a cross-linking agent, wherein said first monomer enhances the bioadhesive properties of said composition.

3. A bioadhesive composition according to claim 2 wherein said first monomer enhances the mechanical strength of said composition and/or said second monomer increases the water activity of said composition.

4. A bioadhesive composition according to claim 3 wherein said second monomer lowers the electrical impedance of said composition and enhances the electrical conductivity of said composition.

5. A bioadhesive composition according to claim 2 wherein said first monomer is a compound of formula

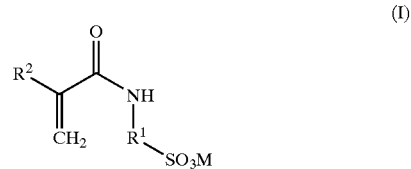

(I)

wherein $R^1$ is an optionally substituted hydrocarbon moiety, $R^2$ is hydrogen or an optionally substituted methyl or ethyl group, and M is hydrogen or a cation.

6. A bioadhesive composition according to claim 5 wherein $R^1$ is an optionally substituted alkyl, cycloalkyl or aromatic moiety containing from 3 to 12 carbon atoms.

7. A bioadhesive composition according to claim 5 wherein $R^1$ is

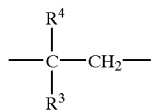

wherein $R^3$ is hydrogen or an optionally substituted straight or branched chain alkyl group possessing from 1 to 6 carbon atoms and $R^4$ is an optionally substituted straight or branched chain alkyl group possessing from 1 to 6 carbon atoms.

8. A bioadhesive composition according to claim 2 wherein said second monomer is a compound of formula

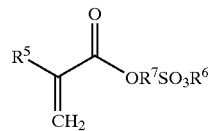

(II)

wherein $R^5$ is hydrogen or optionally substituted methyl or ethyl, $R^6$ is hydrogen or a cation and $R^7$ is an optionally substituted alkylene moiety of 1 to 4 carbon atoms.

9. A bioadhesive composition according to claim 1 which is obtained by polymerising an aqueous reaction mixture comprising a hydrophilic unsaturated water-soluable first monomer, a hydrophilic unsaturated water-soluble second monomer, and a cross-linking agent, wherein said first monomer enhances the bioadhesive properties of the composition.

10. A biomedical electrode which comprises a bioadhesive composition according to claim 1 in association with an electrically conductive interface.

11. A biomedical electrode according to claim 10 which further comprises a support.

12. A fixation product for attaching a biomedical device to the human body, wherein said product comprises a bioadhesive composition of claim 1.

* * * * *

UNITED STATES PATENT AND TRADEMARK OFFICE
CERTIFICATE OF CORRECTION

PATENT NO. : 6,792,301 B2
DATED : September 14, 2004
INVENTOR(S) : Hugh Semple Munro et al.

It is certified that error appears in the above-identified patent and that said Letters Patent is hereby corrected as shown below:

<u>Title page,</u>
Item [63], Related U.S. Application Data, should read -- Continuation of application No. 09/771,018, filed on January 26, 2001, now abandoned, which is a continuation of application No. PCT/GB99/02505, filed on July 30, 1999 --.

Signed and Sealed this

Twenty-fourth Day of May, 2005

JON W. DUDAS
*Director of the United States Patent and Trademark Office*